United States Patent [19]

Kyomura et al.

[11] Patent Number: 5,705,453
[45] Date of Patent: Jan. 6, 1998

[54] INDAZOLE COMPOUNDS AND THE USE THEREOF

[75] Inventors: Nobuo Kyomura; Shuko Okui; Yoshiya Ikeda; Shigeru Suzuki; Hirohumi Tomita; Yoshiaki Higashino, all of Kanagawa, Japan

[73] Assignee: Mitsubishi Chemical Corporation, Tokyo, Japan

[21] Appl. No.: 599,340

[22] Filed: Feb. 8, 1996

[30] Foreign Application Priority Data

Feb. 9, 1995 [JP] Japan ............... 7-021383
Jan. 16, 1996 [JP] Japan ............... 8-004963

[51] Int. Cl.[6] ............ A61K 31/415; A61K 31/505; A01N 43/56; C07D 401/12
[52] U.S. Cl. ............ 504/117; 514/341; 546/275.7
[58] Field of Search ............ 514/341; 546/271; 504/117

[56] References Cited

U.S. PATENT DOCUMENTS

| | | | |
|---|---|---|---|
| 3,457,269 | 7/1969 | Kirchner | 260/295 |
| 3,647,819 | 3/1972 | Kirchner | 260/310 |
| 3,678,059 | 7/1972 | Gschwend et al. | 260/310 |
| 3,681,382 | 8/1972 | Gschwend | 260/310 |
| 3,711,610 | 1/1973 | Kirchner | 424/273 |
| 4,806,554 | 2/1989 | Effland et al. | 514/338 |
| 4,968,805 | 11/1990 | Okada et al. | 546/271 |
| 5,116,835 | 5/1992 | Rüger et al. | 514/218 |

FOREIGN PATENT DOCUMENTS

| | | | |
|---|---|---|---|
| 2 015 568 | 11/1970 | Germany. | |
| 2 135 398 | 1/1972 | Germany. | |
| 9405642 | 3/1994 | Germany | 231/56 |
| 48-81858 | 11/1973 | Japan. | |
| 0329020 | 8/1989 | Japan | 401/12 |
| 1-207 208 | 8/1989 | Japan. | |
| WO94/5642 | 3/1994 | WIPO. | |

OTHER PUBLICATIONS

Darvas et al., Magy. Kem. Lopja., 30(4) pp. 208–215 (1975).

*Primary Examiner*—Johann Richter
*Assistant Examiner*—Jane C. Osweckí
*Attorney, Agent, or Firm*—Wenderoth, Lind & Ponack

[57] ABSTRACT

A indazole compound useful as an agricultural and horticultural insecticide, miticide, and/or fungicide which is represented by the formula set out below, wherein $R^1$ represents hydrogen, a $C_1$-$C_4$ alkyl, a $C_1$-$C_4$ alkoxy, or a halogen; $R^2$ and $R^3$ are preferably hydrogen atoms; and $R^4$ represents, for example, hydrogen, a $C_1$-$C_8$ alkyl, a $C_1$-$C_8$ alkoxy, a halogen, a $C_1$-$C_4$ haloalkoxy, a 5- to 7-membered cycloalkoxy, a $C_1$-$C_4$ alkylthio, a phenylamino, an N-($C_1$-$C_4$ alkyl)-phenylamino, pyrrole-yl, imidazole-yl, pyrrolidino, piperidino, or phenoxy.

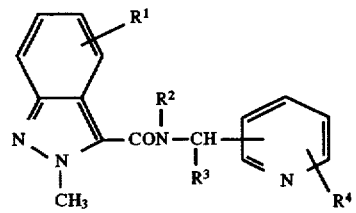

7 Claims, No Drawings

1

INDAZOLE COMPOUNDS AND THE USE THEREOF

BACKGROUND OF THE INVENTION

1. Field of the Invention

The present invention relates to a novel indazole compound. The present invention further relates to an insecticidal, miticidal, and fungicidal composition for use in agriculture and horticulture which comprises the indazole compound as an active ingredient.

2. Related Art

In the field of agriculture and horticulture, various fungicides and insecticides have been developed and practically used so far today for the purpose of controlling numbers of crop diseases and insect pests. However, agricultural and horticultural fungicides and insecticides ordinarily and widely used are not always satisfactory from viewpoints of fungicidal and insecticidal activities, fungicidal and insecticidal spectra, and safety such as residual activities. In addition, they fail to meet requirements of reducing application frequencies and amounts.

The appearance of phytopathogenic fungi and injurious insects which have aquired resistance to ordinary and widely used pesticides also raises a problem. For example, in the cultivations of vegetables, fruit trees, flowers, teas, barleys, wheats, rice and the like, numbers of pathogenic fungi and harmful insects have appeared in various parts of the world, which have acquired resistance to various types of pesticides such as triazole type, imidazole type, pyrimidine type, benzimidazole type, dicarboxyimido type, phenylamido type, and organic phosphorus type. Thus, from year to year, it becomes more difficult to control these pathogenic fungi and harmful insects.

There still remain several pesticides, e.g. dithiocarbamate type and phthalimide type pesticides, to which pathogenic fungi or harmful insects have not yet acquired resistance. However, these pesticides are not preferred in view of environmental pollutions due to their generally high application amounts and frequencies. Accordingly, developments of novel fungicides and insecticides are highly desired which have satisfactory controlling activities, at low application amounts, against various pathogenic fungi or harmful insects that have acquired resistances to ordinary and widely .Used agricultural and horticultural fungicides and insecticides, and also have reduced adverse effects on environment. Furthermore, as regards miticides, developments of miticides are desired which have high safety and excellent controlling effect against mites that have acquired resistances to conventional miticides.

U.S. Pat. No. 3,457,269, U.S. Pat. Nos. 3,647,819, 3,678,059, 3,681,382 and 3,711,610; and disclose indazole derivatives having pharmaceutical activities. However, all of these compounds are 1H derivatives, and none of these documents teaches or suggests that the disclosed indazole derivatives have insecticidal, miticidal or fungicidal activities.

Japanese Patent Unexamined Publication. discloses that esters of 1H-indazole-3-carboxylic acid and carboxamide derivatives (lower-alkylamines as amino moieties) have plant growth regulating activity. However, this publication neither teaches nor suggests insecticidal, miticidal or fungicidal activity of the compounds.

In addition, International Publication WO 94/5642 discloses 2H-indazole-3-carboxamides compounds and their insecticidal, miticidal or fungicidal activity. These compounds are characterized by having aralkylamines as amino moieties. More specifically, this document merely exemplifies benzylamines and naphthalene methylamines which may be substituted. Accordingly, this publication neither teaches nor suggests compounds having heteroaralkylamines as amino moieties as well as processes for preparation and insecticidal, miticidal and fungicidal activities of the compounds.

SUMMARY OF THE INVENTION

An object of the present invention is to provide chemical substances which have high controlling activities against various pathogenic fungi and harmful insects that are resistant to ordinary and widely used agricultural and horticultural fungicides, insecticides and miticides and thus are useful as active ingredients of agricultural and horticultural compositions as fungicides and insecticides. Another object of the present invention is to provide chemical substances useful as active ingredients of agricultural and horticultural compositions as fungicides and insecticides which have the above features and high safeties due to reduced problems of residual toxicities and environmental pollutions. A further object of the present invention is to provide novel indazole derivatives having the aforementioned utilities which have 2H-indazole as acid moieties and pyridylmethylamines as amino moieties.

The inventors of the present invention conducted research to achieve the foregoing objects, and as a result, they found that novel indazole compounds represented by the formula set out below have the aforementioned features. The present invention was achieved on the basis of the findings. The present invention thus provides indazole compounds represented by the following formula (I);

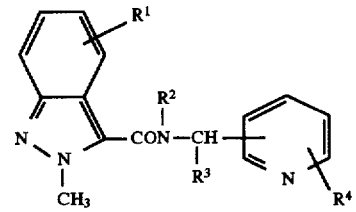

and agricultural and horticultural fungicides, insecticides and miticides which comprise said compounds as active ingredients.

DETAILED DESCRIPTION OF THE INVENTION

In the above formula, $R^1$ represents a hydrogen atom, a $C_1$–$C_4$ alkyl group, a $C_1$–$C_4$ alkoxy group, or a halogen atom; $R^2$ represents a hydrogen atom, a $C_1$–$C_4$ alkyl group, a $C_2$–$C_5$ alkanoyl group, methoxymethyl group, or 2-methoxy ethyl group; $R^3$ represents a hydrogen atom or a $C_1$–$C_4$ alkyl group; $R^3$ represents a hydrogen atom, a $C_1$–$C_8$ alkyl group, a $C_1$–$C_8$ alkoxy group, a halogen atom, a $C_1$–$C_4$ haloalkoxy group, a 5-membered to 7-membered cycloalkoxy group which may be substituted, a $C_1$–$C_4$ alkylthio group, a phenylamino group which may be substituted, an N-($C_1$–$C_4$ alkyl)-phenylamino group, pyrrolyl group, imidazolyl group, pyrrolidino group, a piperidino group which may be substituted, or a phenoxy group which may be substituted (where a functional group selected from the group consisting of cycloalkoxy, phenylamino, piperidino, and phenoxy has two or more substituents on its nucleus, any two adjacent substituents among said substituents may form a ring structure together with two atoms on the nucleus to which the adjacent substituents bind, and said ring structure may further have one or more substitutents on the ring.).

In the general formula (I), $R^1$ may substitute at any position on the phenyl nucleus of the indazole compound. Straight- or branched-chain $C_1$–$C_4$ alkyl groups can be used as the $C_1$–$C_4$ alkyl group represented by $R^1$, and more specifically, such alkyls as methyl group, ethyl group, n-propyl group, isopropyl group, n-butyl group, isobutyl group, sec-butyl group, and t-butyl group may be used. As the $C_1$–$C_4$ alkoxy group, straight- or branched-chain $C_1$–$C_4$ alkoxy groups can be used, and more specifically, such alkoxys as methoxy group, ethoxy group, n-propoxy group, isopropoxy group, n-butoxy group, isobutoxy group, sec-butoxy group, and t-butoxy group may be used. As the halogen atom represented by $R^1$, any one of a fluorine atom, a chlorine atom, a bromine atom, or an iodine atom may be used. Preferably used $R^1$ includes, for example, a hydrogen atom, methyl group, methoxy group, and a chlorine atom. Where $R^1$ is the alkyl group or the alkoxy group, it is preferred that $R^1$ substitues at the 7-position of the nucleus of the indazole compound. Where $R^1$ is a halogen atom, the atom perferably substitutes at the 6- or 7-position of the nucleus of the indazole compound.

The aforementioned alkyls may be used as the $C_1$–$C_4$ alkyl group represented by $R^2$. As the $C_2$–$C_5$ alkanoyl group, straight- or branched-$C_2$–$C_5$ alkanoyl groups can be used, and, for example, acetyl group, propionyl group, n-butyryl group, n-valeryl group, isovaleryl group, 2-methylbutyryl group, and pivaloyl group may be used. Preferred $R^2$ includes, for example, a hydrogen atom, methyl group, ethyl group, methoxymethyl group, and acetyl group. A hydrogen atom is particularly preferred. The compounds having hydrogen atoms as $R^1$ and $R^2$ are preferred embodiments of the present invention.

The above-mentioned alkyls can be used as the $C_1$–$C_4$ alkyl group represented by $R^3$. Preferred $R^3$ include, for example, a hydrogen atom and methyl group. A hydrogen atom is particularly preferred. In the general formula (I), the methylene group attached with $R^3$ and the substituent represented by $R^4$ may substitute at any position of the pyridine nucleus. Preferred compounds are those having the $R^3$-substituted methylene group at the 3-position and $R^4$ at the 6-position of the pyridine ring; those having the $R^3$-substituted methylene group at the 2-position and $R^4$ at the 6-position of the pyridine ring; and those having the $R^3$-substituted methylene group at the 4-position and $R^4$ at the 2-position of the pyridine ring. Particularly preferred compounds are those having the $R^3$-substituted methylene group at the 3-position and $R^4$ at the 6-position of the pyridine ring.

As the $C_1$–$C_8$ alkyl group represented by $R^4$, straight- or branched-chain $C_1$–$C_8$ alkyl groups can be used. For example, alkyls such as methyl group, ethyl group, n-propyl group, isopropyl group, n-butyl group, isobutyl group, sec-butyl group, t-butyl group, n-amyl group, isoamyl group, t-amyl group, n-hexyl group, 1-ethyl-1-methylpropyl group, n-heptyl group, n-octyl group and 2-ethylhexyl group may preferably used. As the $C_1$–$C_8$ alkoxy group represented by $R^4$, alkoxy groups corresponding to the above $C_1$–$C_8$ alkyl groups may be used. Any one of fluorine atom, chlorine atom, bromine atom, or iodine atom may be used as the halogen atom.

As the $C_1$–$C_4$ haloalkoxy group represented by $R^4$, straight- or branched-chain $C_1$–$C_4$ alkoxy groups that are substituted by one or more halogen atoms selected from fluorine atom, chlorine atom, bromine atom or iodine atom can be used. Examples include, for example, monofluoromethoxy group, difluoromethoxy group, trifluoromethoxy group, 2-fluoroethoxy group, 2-chloroethoxy group, 2,2,2-trifluoroethoxy group, 2-chloroethoxy group, 3-chloropropoxy group, 3-bromopropoxy group, 3,3,3-trifluoropropoxy group, 2,2,3,3-tetrafluoropropoxy group, 2,2,3,3,3-pentafluoropropoxy group, 2,2-dichloro-3,3,3-trifluoropropoxy group, 1-trifluoromethylethoxy group, 1,3-difluoro-2-propoxy group, 1,1,1,3,3,3-hexafluoro-2-propoxy group, 4-chlorobutoxy group, 4,4,4-trifluorobutoxy group, 3,3,4,4,4-pentafluorobutoxy group, 2,2,3,3,4,4-hexafluorobutoxy group, 2,2,3,4,4,4-hexafluorobutoxy group, 2,2,3,3,4,4,4-heptafluorobutoxy group, 1-trifluoromethylpropoxy group, 1,1,1,2,2-pentafluoro-3-butoxy group.

As the 5-membered to 7-membered cycloalkoxy group represented by $R^4$, 5 to 7-membered cycloalkoxy groups having one or more (preferably one) substituents such as $C_1$–$C_4$ alkyl groups or one 5 to 7-membered condensed aromatic ring, e.g., a condensed benzene ring as well as unsubstituted 5 to 7-membered cycloalkoxy groups can be used. For example, cyclopentyloxy group, cyclohexyloxy group, cycloheptyloxy group, 2-methylcyclopentyloxy group, 2,4-dimethylcyclopentyloxy group, 2,3,4-trimethylcyclopentyloxy group, 4-methylcyclohexyloxy group, 2,4-dimethylcyclohexyloxy group, 4,4-dimethylcyclohexyloxy group, 1,2,3,4-tetrahydronaphthyl-1-yloxy group, 1,2,3,4-tetrahydronaphthyl-2-yloxy group may be used.

As the $C_1$–$C_4$ alkylthio group represented by $R^4$, straight- or branched-chain $C_1$–$C_4$ alkylthio groups can be used, and more specifically, methylthio group, ethylthio group, n-propylthio group, isopropylthio group, n-butylthio group, isobutylthio group, sec-butylthio group, t-butylthio group and the like may be used. The phenyl amino group represented by $R^4$ may have a $C_1$–$C_4$ alkyl group, preferably a methyl group, on the nitrogen atom, and may have one or more (preferably one) halogen atoms or one or more (preferably one) $C_1$–$C_4$ haloalkyl groups on the benzene nucleus. The piperidino group represented by $R^4$ may have one condensed benzene ring on its nucleus and may form, for example, 1,2,3,4-tetrahydroquinoline-1-yl group or 1,2,3,4-tetrahydroisoquinoline-2-yl group.

When $R^4$ is a phenoxy group, the phenoxy group may have from one to three (preferably two or three) substituents selected from the group consisting of a $C_1$–$C_8$ alkyl group, a $C_1$–$C_8$ alkoxy group, a halogen atom, nitro group, cyano group, a $C_1$–$C_4$ haloalkyl group, a $C_1$–$C_4$ haloalkoxy group, phenyl group, phenoxy group, a $C_2$–$C_5$ alkanoyl group whose oxo group may be protected by a ketal group, benzoyl group, a $C_1$–$C_4$ alkoxycarbonyl group, a $C_1$–$C_4$ alkylthio group, trifluoromethylthio group, and methylenedioxy group. Where the phenoxy group has two or three substituents, the substitutents may be the same or different.

As the substituents on the phenoxy group, $C_1$–$C_4$ alkyl group, the $C_1$–$C_8$ alkoxy group, the halogen atom, and the $C_1$–$C_8$ alkoxy group as described above may be used. As the $C_2$–$C_5$ alkanoyl group, those mentioned above may be used. In addition, those having an oxo group protected by a ketal group, preferably a cyclic ketal group, may also be used. For example, acetyl group protected by ethyenedioxyketal group or the like may be used.

As the $C_1$–$C_4$ haloalkyl group, straight- or branched-chain $C_1$–$C_4$ alkyl groups substituted with one or more halogen atoms selected from fluorine atom, chlorine atom, bromine atom, or iodine atom can be used. Examples include, for example, monofluoromethyl group, difluoromethyl group, trifluoromethyl group, 2-fluoroethyl group, 2-chloroethyl group, 2,2,2-trifluoroethyl group, 2-chloroethyl group, 3-chloropropyl group, 3-bromopropyl group, 3,3,3-trifluoropropyl group, 2,2,3,3-tetrafluoropropyl group, 2,2,3,3,3-pentafluoropropyl group, 2,2-dichloro-3,3,3-trifluoropropyl group, 1-trifluoromethyl-ethyl group, 1,3-difluoro-2-propyl group, 1,1,1,3,3,3-hexafluoro-2-propyl group, 4-chlorobutyl group, 4,4,4-trifluorobutyl group, 3,3,4,4,4-pentafluorobutyl group, 2,2,3,3,4,4-hexafluorobutyl group, 2,2,3,4,4,4-hexafluorobutyl group, 2,2,3,3,4,4,4-heptafluorobutyl group, 1-trifluoromethylpropyl group, and 1,1,1,2,2-pentafluoro-3-butyl group.

As the $C_1$–$C_4$ alkoxycarbonyl group, carbonyl groups substituted with the above-described $C_1$–$C_4$ alkoxy groups can be used, and more specifically, methoxycarbonyl group, ethoxycarbonyl group, n-propoxycarbonyl group, isopropoxycarbonyl group, n-butoxycarbonyl group, isobutoxycarbonyl group, sec-butoxycarbonyl group, and t-butoxycarbonyl group may be used. As the $C_1$–$C_4$ alkylthio group, the above-described $C_1$–$C_4$ alkylthio groups can be used, and more specifically, methylthio group, ethylthio group, n-propylthio group, isopropylthio group, n-butylthio group, isobutylthio group, sec-butylthio group, and t-butylthio group may be used.

The benzene nucleus of the phenoxy group represented by $R^4$ may have one condensed benzene ring. One or two, preferably one halogen atom, or alternatively, one or two, preferably one $C_1$–$C_4$ alkoxy group may substitute on the condensed benzene ring. Examples of such groups include, for example, 1-naphthoxy group, 2-naphthoxy group, and 6-bromo-2-naphthoxy group. In addition, the benzene nucleus of the phenoxy group may further have one condensed saturated furan ring. One or two, preferably two $C_1$–$C_4$ alkyl groups may substitute on the furan ring. An example of the group is 2,3-dihydro-2,2-dimethyl-benzo[b]furan-7-yl-oxy group.

Examples of preferred $R^4$ include, for example, n-propyl group, n-butyl group, iso-butyl group, n-pentyl group, n-propoxy group, cyclopentyloxy group, cyclohexyloxy group, 3-methylcyclohexyloxy group, cycloheptyloxy group, 2,2,2-trifluoro-1-methylethyloxy group, 3,3,3-trifluoropropyl group, 2,2,3,3-tetrafluoropropyl group, chlorine atom, unsubstituted phenoxy group, 4-methylphenoxy group, 3-methylphenoxy group, 4-ethylphenoxy group, 3-ethylphenoxy group, 3-isopropylphenoxy group, 3-tert-butylphenoxy group, 4-methoxyphenoxy group, 3-methoxyphenoxy group, 3-n-butoxyphenoxy group, 3-trifluoromethyloxyphenoxy group, 3-phenyloxyphenoxy group, 4-chlorophenoxy group, 3-chlorophenoxy group, 4-fluorophenoxy group, 3-fluorophenoxy group, 4-bromophenoxy group, 3-bromophenoxy group, 4-trifluoromethylphenoxy group, 3-trifluoromethylphenoxy group, 2-trifluoromethylphenoxy group, 3-phenylphenoxy group, 3-acetylphenoxy group, 4-methoxycarbonylphenoxy group, 4-methylthiophenoxy group, 3-nitrophenoxy group, 3,4-methylenedioxyphenoxy group, 2-naphthoxy group, and 6-bromo-2-naphthoxy group.

Some of the indazole derivatives of the present invention have one or two asymmetric carbon atoms in their molecules depending on structures of $R^1$ through $R^4$. Any optical isomers derived from one or more such asymmetric carbon atoms and diastereoisomers derived from two or more asymmetric carbon atoms, any mixtures of the foregoing isomers, and racemates fall within the scope of the present invention. Furthermore, some of the compounds of the present invention can form acid addition salts with inorganic acids such as hydrochloric acid, sulfuric acid, phosphoric acid, and nitric acid, or organic acids such as oxalic acid, citric acid, tartaric acid, and malic acid. Such acid addition salts also fall within the scope of the present invention. In addition, any hydrates and solvates also fall within the scope of the invention.

The compound of the present invention represented by the general formula (I) can be prepared, for example, according to the scheme set out below, which includes the step of reacting a compound of formula (II) with a compound of formula (III) in the presence or absence of a solvent and preferably in the presence of a base. In the formulas (II) and (III), $R^1$, $R^2$, $R^3$ and $R^4$ are the same as those defined above, and Z represents a chlorine atom, a bromine atom, hydroxy group, methoxy group, ethoxy group, or propoxy group.

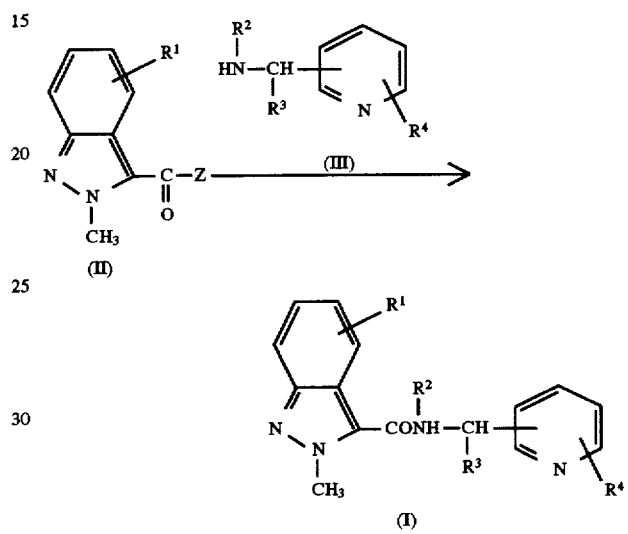

More specifically, where Z of the compound of general formula (II) is a chlorine atom or bromine atom, solvents, for example, aromatic hydrocarbons such as benzene, toluene, and xylene; ketones such as acetone, methyl ethyl ketone, and methyl isobutyl ketone; halogenated hydrocarbons such as chloroform and methylene chloride; water; esters such as methyl acetate and ethyl acetate; and polar solvents such as tetrahydrofuran, acetonitrile, dioxane, N,N-dimethylformamide, N-methylpyrrolidone and dimethyl sulfoxide may be used. The reaction may be carried out at a temperature of from 0° to 30°, preferably from 0° to 5°, in the presence of a base. As the base, for example, sodium hydroxide, potassium hydroxide, sodium carbonate, potassium carbonate, pyridine may be used.

Where Z of the compound of general formula (II) is hydroxy group, methoxy group, ethoxy group, or propoxy group, the reaction may be carried out at a temperature of from 150° to 250°, preferably from 200° to 250° C. in the absence of a solvent, or alternatively, using a solvent having a high boiling point, e.g. N,N-dimethylformamide, N-methylpyrrolidone, and dimethyl sulfoxide. The compounds represented by general formula (II) and general formula (III) can be prepared by methods which are known to those skilled in the art.

Compounds No.1 through 200 are specifically described below as examples of preferred compounds of the present invention, where each of the compounds has $R^3$-substituted methylene group at the 3-position and $R^4$ at the 6-position on the pyridine nucleus. However, the compounds of the present invention are not limited to these examples. The abbreviations in the table are Me: methyl group; Et: ethyl group; Pr: propyl group; Bu: butyl group; and Ph: phenyl group. For example, $R^1$:-7-Me represents that $CH_3$— as $R^1$ substitutes on the 7-position of the nucleus of the indazole compound, and R⁴:3-(O—n—Bu)-phenoxy and 4-CF₃-phenoxy represent phenoxy groups whose benzene rings are substituted with normal butoxy group at the 3-position and trifluoromethyl group at the 4-position as R⁴s, respectively.

TABLE 1

| No. | $R^1$ | $R^2$ | $R^3$ | $R^4$ | No. | $R^1$ | $R^2$ | $R^3$ | $R^4$ |
|---|---|---|---|---|---|---|---|---|---|
| 1 | —H | —H | —H | —Me | 101 | —H | —H | —Me | —Me |
| 2 | —H | —H | —H | —Et | 102 | —H | —H | —Me | —Et |
| 3 | —H | —H | —H | -n-Pr | 103 | —H | —H | —Me | -n-Pr |
| 4 | —H | —H | —H | -iso-Pr | 104 | —H | —H | —Me | -iso-Pr |
| 5 | —H | —H | —H | -n-Bu | 105 | —H | —H | —Me | -n-Bu |
| 6 | —H | —H | —H | -iso-Bu | 106 | —H | —H | —Me | -iso-Bu |
| 7 | —H | —H | —H | -n-C₅H₁₁ | 107 | —H | —H | —Me | -n-C₅H₁₁ |
| 8 | —H | —H | —H | —OMe | 108 | —H | —H | —Me | —OMe |
| 9 | —H | —H | —H | —OEt | 109 | —H | —H | —Me | —OEt |
| 10 | —H | —H | —H | —O-n-Pr | 110 | —H | —H | —Me | —O-n-Pr |
| 11 | —H | —H | —H | —O-iso-Pr | 111 | —H | —H | —Me | —O-iso-Pr |
| 12 | —H | —H | —H | —O-tert-Bu | 112 | —H | —H | —Me | —O-tert-Bu |
| 13 | —H | —H | —H | —Cl | 113 | —H | —H | —Me | —Cl |
| 14 | —H | —H | —H | —F | 114 | —H | —H | —Me | —F |
| 15 | —H | —H | —H | —O—CH(CF₃)Me | 115 | —H | —H | —Me | —O—CH(CF₃)Me |
| 16 | —H | —H | —H | —O—CH₂CF₂CHF₂ | 116 | —H | —H | —Me | —O—CH₂CF₂CHF₂ |
| 17 | —H | —H | —H | —O—CH₂CF₂CF₃ | 117 | —H | —H | —Me | —O—CH₂CF₂CF₃ |
| 18 | —H | —H | —H | cyclopentoxy | 118 | —H | —H | —Me | cyclopentoxy |
| 19 | —H | —H | —H | cyclohexoxy | 119 | —H | —H | —Me | cyclohexoxy |
| 20 | —H | —H | —H | cycloheptoxy | 120 | —H | —H | —Me | cycloheptoxy |
| 21 | —H | —H | —H | 3-Me-cyclo-hexyloxy | 121 | —H | —H | —Me | 3-Me-cyclo-hexylosy |
| 22 | —H | —H | —H | —SMe | 122 | —H | —H | —Me | —SMe |
| 23 | —H | —H | —H | —NH—Ph | 123 | —H | —H | —ME | —NH—Ph |
| 24 | —H | —H | —H | —NH-3-Cl—Ph | 124 | —H | —H | —Me | —NH-3-Cl—Ph |
| 25 | —H | —H | —H | —NH-3-CF₃—Ph | 125 | —H | —H | —mE | —NH-3-CF₃—Ph |
| 26 | —H | —H | —H | —NH-4-CF₃—Ph | 126 | —H | —H | —mE | —NH-4-CF₃—Ph |
| 27 | —H | —H | —H | —N(CH₃)—Ph | 127 | —H | —H | —Me | —N(CH₃)—Ph |
| 28 | —H | —H | —H | -Pyrrolyl | 128 | —H | —H | —Me | -Pyrrolyl |
| 29 | —H | —H | —H | -Imidazolyl | 129 | —H | —H | —Me | -Imidazolyl |
| 30 | —H | —H | —H | -Pyrrolidino | 130 | —H | —H | —Me | -Pyrrolidino |
| 31 | —H | —H | —H | -Piperidino | 131 | —H | —H | —Me | -Piperidino |
| 32 | —H | —H | —H | -(1,2,3,4-tetrahydroisoquinoline)-2-yl | 132 | —H | —H | —Me | -(1,2,3,4-tetrahydroisoquinoline)-2-yl |
| 33 | —H | —H | —H | -O-Ph | 133 | —H | —H | —Me | -O-Ph |
| 34 | —H | —H | —H | 4-Me-phenoxy | 134 | —H | —H | —Me | 4-Me-phenoxy |
| 35 | —H | —H | —H | 3-Me-phenoxy | 135 | —H | —H | —Me | 3-Me-phenoxy |
| 36 | —H | —H | —H | 3,4-di-Me-phenoxy | 136 | —H | —H | —Me | 3,4-di-Me-phenoxy |
| 37 | —H | —H | —H | 3,5-di-Me-phenoxy | 137 | —H | —H | —Me | 3,5-di-Me-phenoxy |
| 38 | —H | —H | —H | 3,4,5-tri-Me-phenoxy | 138 | —H | —H | —Me | 3,4,5-tri-Me-phenoxy |
| 39 | —H | —H | —H | 4-Et-phenoxy | 139 | —H | —H | —Me | 4-Et-phenoxy |
| 40 | —H | —H | —H | 3-Et-phenoxy | 140 | —H | —H | —Me | 3-Et-phenoxy |
| 41 | —H | —H | —H | 3-(iso-Pr)-phenoxy | 141 | —H | —H | —Me | 3-(iso-Pr)-phenoxy |
| 42 | —H | —H | —H | 3,5-di-iso-Pro-phenoxy | 142 | —H | —H | —Me | 3,5-di-iso-Pro-phenoxy |
| 43 | —H | —H | —H | 3-(tert-Bu)-phenoxy | 143 | —H | —H | —Me | 3-(tert-Bu)-phenoxy |
| 44 | —H | —H | —H | 4-OMe-phenoxy | 144 | —H | —H | —Me | 4-OMe-phenoxy |
| 45 | —H | —H | —H | 3-OMe-phenoxy | 145 | —H | —H | —Me | 3-OMe-phenoxy |
| 46 | —H | —H | —H | 2-OMe-phenoxy | 146 | —H | —H | —Me | 2-OMe-phenoxy |
| 47 | —H | —H | —H | 2,3-di-OMe-phenoxy | 147 | —H | —H | —Me | 2,3-di-OMe-phenoxy |
| 48 | —H | —H | —H | 3-OEt-phenoxy | 148 | —H | —H | —Me | 3-OEt-phenoxy |
| 49 | —H | —H | —H | 4-(O-n-Bu)-phenoxy | 149 | —H | —H | —Me | 4-(O-n-Bu)-phenoxy |
| 50 | —H | —H | —H | 3-(O-n-Bu)-phenoxy | 150 | —H | —H | —Me | 3-(O-n-Bu)-phenoxy |

TABLE 1-continued

| No. | R¹ | R² | R³ | R⁴ | No. | R¹ | R² | R³ | R⁴ |
|---|---|---|---|---|---|---|---|---|---|
| 51 | —H | —H | —H | 2-(O-n-Bu)-phenoxy | 151 | —H | —H | —Me | 2-(O-n-Bu)-phenoxy |
| 52 | —H | —H | —H | 4-Cl-phenoxy | 152 | —H | —H | —Me | 4-Cl-phenoxy |
| 53 | —H | —H | —H | 3-Cl-phenoxy | 153 | —H | —H | —Me | 3-Cl-phenoxy |
| 54 | —H | —H | —H | 2-Cl-phenoxy | 154 | —H | —H | —Me | 2-Cl-phenxoy |
| 55 | —H | —H | —H | 3,4-di-Cl-phenoxy | 155 | —H | —H | —Me | 3,4-di-Cl-phenoxy |
| 56 | —H | —H | —H | 2,4-di-Cl-phenoxy | 156 | —H | —H | —Me | 2,4-di-Cl-phenoxy |
| 57 | —H | —H | —H | 2,3,4-tri-Cl-phenoxy | 157 | —H | —H | —Me | 2,3,4-tri-Cl-phenoxy |
| 58 | —H | —H | —H | 3-Br-phenoxy | 158 | —H | —H | —Me | 3-Br-phenxoy |
| 59 | —H | —H | —H | 4-F-phenoxy | 159 | —H | —H | —Me | 4-F-phenoxy |
| 60 | —H | —H | —H | 3-F-phenoxy | 160 | —H | —H | —Me | 3-F-phenoxy |
| 61 | —H | —H | —H | 2-F-phenoxy | 161 | —H | —H | —Me | 2-F-phenoxy |
| 62 | —H | —H | —H | 3-Cl-4-F-phenoxy | 162 | —H | —H | —Me | 3-Cl-4-4F-phenoxy |
| 63 | —H | —H | —H | 3-Cl-4,5-di-F phenoxy | 163 | —H | —H | —Me | 3-Cl-4,5-di-F phenoxy |
| 64 | —H | —H | —H | 4-NO₂-phenoxy | 164 | —H | —H | —Me | 4-NO₂-phenoxy |
| 65 | —H | —H | —H | 3-NO₃-phenoxy | 165 | —H | —H | —Me | 3-NO₃-phenoxy |
| 66 | —H | —H | —H | 2-NO₂-phenoxy | 166 | —H | —H | —Me | 2-NO₃-phenoxy |
| 67 | —H | —H | —H | 4-CN-phenoxy | 167 | —H | —H | —Me | 4-CN-phenoxy |
| 68 | —H | —H | —H | 3-CN-phenoxy | 168 | —H | —H | —Me | 3-CN-phenoxy |
| 69 | —H | —H | —H | 2-CN-phenoxy | 169 | —H | —H | —Me | 2-CN-phenoxy |
| 70 | —H | —H | —H | 4-CF₃-phenoxy | 170 | —H | —H | —Me | 4-CF₃-phenoxy |
| 71 | —H | —H | —H | 3-CF₃-phenoxy | 171 | —H | —H | —Me | 3-CF₃-phenoxy |
| 72 | —H | —H | —H | 2-CF₃-phenoxy | 172 | —H | —H | —Me | 2-CF₃-phenoxy |
| 73 | —H | —H | —H | 4-OCF₃-phenoxy | 173 | —H | —H | —Me | 4-OCF₃-phenoxy |
| 74 | —H | —H | —H | 3-OCF₃-phenoxy | 174 | —H | —H | —Me | 3-OCF₃-phenoxy |
| 75 | —H | —H | —H | 2-OCF₃-phenoxy | 175 | —H | —H | —Me | 2-OCF₃-phenoxy |
| 76 | —H | —H | —H | 4-OCHF₂-phenoxy | 176 | —H | —H | —Me | 4-OCHF₂-phenoxy |
| 77 | —H | —H | —H | 3-OCHF₂-phenoxy | 177 | —H | —H | —Me | 3-OCHF₂-phenoxy |
| 78 | —H | —H | —H | 3-OCH₂F-phenoxy | 178 | —H | —H | —Me | 3-OCH₂F-phenoxy |
| 79 | —H | —H | —H | 4-Ph-phenoxy | 179 | —H | —H | —Me | 4-Ph-phenoxy |
| 80 | —H | —H | —H | 3-Ph-phenoxy | 180 | —H | —H | —Me | 3-Ph-phenoxy |
| 81 | —H | —H | —H | 2-Ph-phenoxy | 181 | —H | —H | —Me | 2-Ph-phenoxy |
| 82 | —H | —H | —H | 4-OPh-phenoxy | 182 | —H | —H | —Me | 4-OPh-phenoxy |
| 83 | —H | —H | —H | 3-OPh-phenoxy | 183 | —H | —H | —Me | 3-OPh-phenoxy |
| 84 | —H | —H | —H | 2-OPh-phenoxy | 184 | —H | —H | —Me | 2-OPh-phenoxy |
| 85 | —H | —H | —H | 4-COMe-phenoxy | 185 | —H | —H | —Me | 4-COMe-phenoxy |
| 86 | —H | —H | —H | 3-COMe-phenoxy | 186 | —H | —H | —Me | 3-COMe-phenoxy |
| 87 | —H | —H | —H | 3-COMe-phenoxy ethylenedioxyketal | 187 | —H | —H | —Me | 3-COMe-phenoxy ethylenedioxyketal |
| 88 | —H | —H | —H | 4-COPh-phenoxy | 188 | —H | —H | —Me | 4-COPh-phenoxy |
| 89 | —H | —H | —H | 4-COOMe-phenoxy | 189 | —H | —H | —Me | 4-COOMe-phenoxy |
| 90 | —H | —H | —H | 3-COOMe-phenoxy | 190 | —H | —H | —Me | 3-COOMe-phenoxy |
| 91 | —H | —H | —H | 4-SMe-phenoxy | 191 | —H | —H | —Me | 4-SMe-phenoxy |
| 92 | —H | —H | —H | 3-SMe-phenoxy | 192 | —H | —H | —Me | 3-SME-phenoxy |
| 93 | —H | —H | —H | 4-SCF₃-phenoxy | 193 | —H | —H | —Me | 4-SCF₃-phenoxy |
| 94 | —H | —H | —H | 3-SCF₃-phenoxy | 194 | —H | —H | —Me | 3-SCF₃-phenoxy |
| 95 | —H | —H | —H | 3,4-methylenedioxy-phenoxy | 195 | —H | —H | —Me | 3,4-methylenedioxy-phenoxy |
| 96 | —H | —H | —H | 2-naphthoxy | 196 | —H | —H | —Me | 2-naphthoxy |
| 97 | —H | —H | —H | 1-naphthoxy | 197 | —H | —H | —Me | 1-naphthoxy |
| 98 | —H | —H | —H | 6-Br-2-naphthoxy | 198 | —H | —H | —Me | 6-Br-2-naphthoxy |
| 99 | —H | —H | —H | 6-Cl-2-naphthoxy | 199 | —H | —H | —Me | 6-Cl-2-naphthoxy |
| 100 | —H | —H | —H | 6-OMe-2-naphthoxy | 200 | —H | —H | —Me | 6-OMe-2-naphthoxy |

Compounds having the same $R^2$, $R^3$, and $R^4$ as those of the above-described Compounds No.1 to 200 and its $R^1$ being 4-Cl, 5-Cl, 6Cl, 7-Cl, 7-Me, or 7-OMe; and compounds having the same $R^1$, $R^3$, and $R^4$ as those of each of the above-described compounds and its $R^2$ being Me, Et, —CH$_2$OCH$_3$, or —COCH are also preferred. In addition, also preferred are compounds having the same $R^1$, $R^2$, $R^3$ and $R^4$ as those of the above-described compounds and having the $R^3$-substituted methylene group at the 2-position of the pyridine nucleus and $R^4$ at the 6-position; and compounds having the same $R^1$, $R^2$, $R^3$ and $R^4$ as those of the above-mentioned compounds and having $R^3$-substituted methylene group at the 4-position of the pyridine nucleus and $R^4$ at the 2-position. The compounds listed in Table 2 set out in Examples are also preferred compounds of the present invention.

The compounds of the present invention represented by general formula (I) have potent controlling activities against kinds of insects, mites, and pathogenic fungi of agricultural and horticultural plants. Thus, the compounds of the present invention are useful as active ingredients of agricultural and horticultural pesticides, e.g. agricultural and horticultural fungicides, insecticides, and miticides.

The compounds of the present invention have potent fungicidal activity against phytopathogenic fungi such as Piricularia (Blast causing fungi); Puccinia (Rust causing fungi); Phytophthora; Erysiphe (Downy mildew causing fungi), and thus are useful as active ingredients of agricultural and horticultural fungicides. The compounds of the present invention have high controlling activities against insects belonging to Hemiptera such as, for example, Delphacidae whose examples including, for example, *Sogatella furcifera*, *Nilaparvata lugens*, and *Laodelphax striatellus*, Deltocephalidae whose examples including, for example, *Nephotellix cincticeps* and *Cicadella viridis*, and Aphididae whose examples including, for example, *Myzus persicae*; Lepidoptera such as, for example, *Spodontera lithura*, *Chilo suppresalis*, *Cnaphalocrocis medinalis*, and *Plutella xylostella*; Coleoptera such as, for example, *Callosobruchus chinensis*; Diptera such as, for example, *Musca domestica*, *Aedes aegypti*, and *Culex pipiens molestus*;and Orthoptera. In addition, they have high controlling activities against eggs and larvas of Acarina such as, for example, *Tetranychus urticae*, *Tetranychus cinnabarinns*, and *Panoychus citri*.Accordingly, the compounds are also useful as active ingredients of agricultural and horticultural insecticides and miticides. However, phytopathogenic fungi, insects, and mites which can be controlled by the compounds of the present invention are not limited to those mentioned above as examples.

Where the compounds of the present invention represented by general formula (I) are used as agricultural and horticultural fungicides, insecticides, and/or miticides, the compounds, per se, may be used. Preferably, agricultural and horticultural fungicides, insecticides, and/or miticides in the form of compositions may be used, which can be prepared by using pesticidal adjuvants widely used in the agrochemical art. Although the forms of agricultural and horticultural fungicides, insecticides, and/or miticides are not particularly limited, forms such as emulsifiable concentrates, wettable powder, dust, flowable products, fine particles, granules, tablets, oil solutions, spray liquids, fumigants are preferred. One or more of the compounds of the present invention as described above may be formulated as the active ingredient.

The pesticidal adjuvants for the preparation of the aforementioned agricultural and horticultural fungicides, insecticides, and/or miticides may be used, for example, to improve pesticidal activities and to increase stabilities and dispersabilities of the agricultural and horticultural fungicides, insecticides, and/or miticides. For example, carriers (diluents), spreaders, emulsifying agents, wetting-out agents, dispersing agents, and disintegrating agents may be used.

Examples of the liquid carriers include, for example, water; aromatic hydrocarbons such as toluene and xylene; alcohols such as methanol, butanol, and glycol; ketones such as acetone; amides such as dimethylformamide; sulfoxides such as dimethylsulfoxide; methylnaphtalene; cyclohexane; animal oils; vegetable oils; and fatty acids. As the solid carriers, clay, kaolin, talc, diatomaceous earth, silica, calcium carbonate, montmorillonite, bentonite, feldspar, quartz, alumina, wood shavings, nitrocellulose, starch, and gummi arabiacum may be used.

As the emulsifying agents and the dispersing agents, ordinary surface active agents may be used. For example, anionic surfactants such as, for example, higher alcohol sodium sulfate, stearyl trimethylammonium chloride, polyoxyethylene alkylphenyl ether, and lauryl betaine; cationic surfactants; nonionic surfactants; and amphoteric surfactants may be used. Spreaders such as polyoxyethylene nonylphenyl ether and polyoxyethylene lauryl ether; wetting-out agents such as polyoxyethylene nonylphenyl ether and dialkylsulfosuccinate; fixing agents such as carboxymethyl cellulose and polyvinyl alcohol; and disintegrating agents such as sodium lignosulfonate and sodium lauryl sulfate may also be used.

Contents of the active ingredients of the agricultural and horticultural fungicides, insecticides, and/or miticides of the present invention can generally be chosen between the range of from 0.1 to 99.5 % by weight, which may be appropriately determined depending on various factors such as the forms of the compositions and methods of applications. For example, the compositions may be prepared so as to contain the active ingredient at about 0.5 to 20% by weight, preferably 1 to 10% by weight for dusts; about 1 to 90% by weight, preferably 10 to 80% by weight for wettable powders; and about 1 to 90% by weight, preferably 10 to 40% by weight for emulsifiable concentrates.

For example, where emulsifiable concentrates are used, neat stock concentrates can be prepared by mixing solvents, surfactants and the like to the aforementioned compounds as the active ingredients, and the resulting neat concentrates can be diluted with water to prescribed concentrations before use and then applied. Where wettable powders are used, neat stock compositions can be prepared as the mixture of the aforementioned compounds as the active ingredients, solid carriers, surfactant and the like, and the resulting stock compositions can be diluted to prescribed concentrations before use and then applied. Dusts may be prepared by mixing the above compounds as the active ingredients with solid carriers and the like, and the resulting mixture, per se, may be applied. Granules can be prepared by granulations of mixtures of the above compounds as active ingredients, solid carriers, surfactant and the like, and the resulting compositions, per se, may be applied. Methods for preparations of the compositions in the aforementioned forms are not limited to those set out above, and the processes may appropriately be chosen by ordinary artisens depending on, for example, the types of the active ingredients and the purposes of applications.

Agricultural and horticultural fungicides, insecticides, and/or miticides of the present invention may optionally contain, in addition to the compounds of the present invention as the active ingredients, other active ingredients such as, for example, other fungicides, insecticides, miticides, herbicides, insect growth regulators, fertilizers, soil conditioners. Methods of applications agricultural and horticultural fungicides, insecticides and/or miticides of the present invention are not particularly limited. Any routs of applications may be used, which include, for example, foliar sprays, water surface treatments, soil treatments, and seed treatments. For example, when foliar sprays are employed, solutions at concentrations of from 5 to 1,000 ppm, preferably from 10 to 500 ppm, may be applied at amounts of from 100 to 200 liters/10a. Application amounts for water surface treatments are generally 1 to 10 kg/10a using granules containing 5 to 15% by weight of the active ingredients. For soil treatments, solutions at concentrations of from 5 to 1,000 ppm may be applied at amounts of from 1 to 10 liter/m$^2$. For seed treatments, solutions at concentrations of from 10 to 1,000 ppm may be applied at amounts of from 10 to 100 ml per 1 kg of seeds.

EXAMPLES

The present invention will be further explained by examples. However, the scope of the present invention is not limited to the examples set out below.

Example 1

Preparation of N-[( 6-n-butyl-3-pyridyl)-methyl]-2-methyl-3-indazolecarboxamide

2-Methylindazole-3-carboxylic acid (3.2 g) and thionyl chloride (5.3 g) were heated under reflux for 1 hour. After thionyl chloride was evaporated under reduced pressure, the residue was dissolved in toluene (20 ml). This solution was added dropwise to a solution of 5-aminomethyl-2-n-butylpyridine (3.0 g) and triethylamine (1.9 g) in toluene (30 ml) at 0° to 10° C. After the dropwise addition, the mixture was stirred for 2 hours at room temperature, and then, poured into ice water and extracted with toluene. The toluene layer was successively washed with an aqueous solution of sodium carbonate, water, and saturated aqueous sodium chloride. After drying over anhydrous sodium sulfate, the solvent was evaporated under reduced pressure. The residue was purified column chromatography on silica gel to afford the title compound (5.86 g) shown in Table 2 as No.A. The results of NMR and IR analyses of this compound were as follows:

$^1$H-NMR(CDCl$_3$) δppm : 0.94(3H,t),1.38(2H,q),1.71(2H, m), 2.80(2H,t),4.49(3H,s),4.72(2H,d),6.55(1H,b),7.18(1H, d), 7.25(1H,m),7.33(1H,t),7.61(1H,d),7.67(1H,d) IR(KBr) vcm$^{31\ 1}$: 3260, 2960, 1640, 1540, 1390, 1230, 740

Example 2

Preparation of N-[(6- (4-methylphenoxy )-3-pyridyl-methyl]-2-methyl-3-indazolecarboxamide 2-Methylindazole-3-carboxylic acid (3.2 g) and thionyl chloride ( 5.3 g ) were heated under reflux for 1 hour. After thionyl chloride was evaporated under reduced pressure, the residue was dissolved in toluene (20 ml). This solution was added dropwise to a solution of 5-aminomethyl-2-(4-methylphenoxy)-pyridine (3.9 g) and triethylamine (1.9 g) in toluene (30 ml) at 0° to 10 ° C. After the dropwise addition, the mixture was stirred for 2 hours at room temperature, and then, poured into ice water and extracted with toluene. The toluene layer was washed successively with an aqueous solution of sodium carbonate, water, and saturated aqueous sodium chloride. After drying over anhydrous sodium sulfate, the solvent was evaporated under reduced pressure. The residue was purified by column chromatography on silica gel to afford the title compound (5.83 g) shown in Table 2 as No. A-12. The results of NMR and IR analyses of this compound were as follows.

$^1$H-NMR(CDCl$_3$) δppm : 2.35(3H,t),4.49(3H,s),4.67(2H, d), 6.46(1H,bs),6.91(1H,d),7.02(2H,d),7.21(3H,m),7.34 (1H,m), 7.60(1H,d),7.78(2H,m),8.22(1H,d) IR(KBr) vcm$^{-1}$: 3300, 1650, 1550, 1485, 1295

Example 3

Preparation of N-[(6-phenylamino-3-pyridyl)-methyl]-2-methyl-3-indazolecarboxamide 2-Methylindazole-3-carboxylic acid (3.2 g) and thionyl chloride (5.3 g) were heated under reflux for 1 hour. After thionyl chloride was removed under reduced pressure, the residue was dissolved in tetrahydrofuran (20 ml). This solution was added dropwise to a solution of 5-aminomethyl-2-phenylaminopyridine (3.6 g) and triethylamine (1.9 g) in tetrahydrofuran (30 ml) at 0° to 10° C. After the dropwise addition, the mixture was stirred for 2 hours at room temperature, and then, poured into ice water and extracted with ethyl acetate. The ethyl acetate layer was washed successively with an aqueous solution of sodium carbonate, water, and saturated aqueous sodium chloride. After dryness over anhydrous sodium sulfate, the solvent was evaporated under reduced pressure. The residue was purified column chromatography on silica gel to afford the titled compound (5.37 g) shown in Table 2 as No. A-75. The results of NMR and IR analyses of this compound were as follows.

$^1$H-NMR(CDCl$_3$) δppm : 4.50(3H, s),4.66(2H,d),5.77 (1H,s), 6.41(1H,b),6.95(1H,t),7.09(4H,m),7.18–7.37(6H,m) ,7.61(1H,d), 7.77(1H,d) IR(KBr) vcm$^{-1}$: 3310, 1635, 1620, 1608, 1520, 1495, 1325, 1225, 750, 740, 730, 510

Example 4

The compounds listed in Table 2 were obtained according to the methods of Examples 1–3. In the table, A, B, and C series of compounds are as set out below, and physicochemical properties except melting points are refractive indexes ($n^2_D$, with asterisks). The abbreviations in the table are the same as those used in Table 1.

TABLE 2

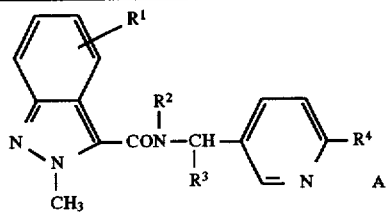
A

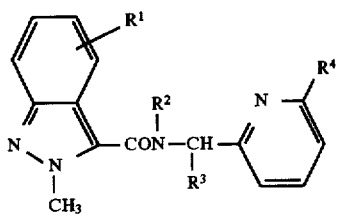
B

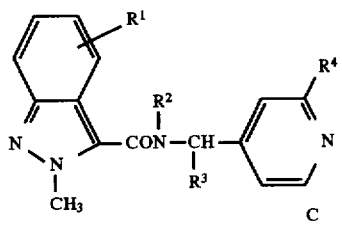
C

| Compound | R¹ | R² | R³ | R⁴ | m.p. (°C.) |
|---|---|---|---|---|---|
| A-1 | —H | —H | —H | -n-Pr | 124–126 |
| A-2 | —H | —H | —H | -n-Bu | 65–66 |
| A-3 | —H | —H | —H | -iso-Bu | 93–95 |
| A-4 | —H | —H | —H | -n-C₅H₁₁ | 106–108 |
| A-5 | —H | —H | —H | —O-n-Pr | 105–107 |
| A-6 | —H | —H | —H | —O-tert-Bu | 155–157 |
| A-7 | —H | —H | —H | cyclopentyloxy | 129–130 |
| A-8 | —H | —H | —H | cyclohexyloxy | 148–149 |
| A-9 | —H | —H | —H | 3-Me-cyclohexyloxy | 112–114 |
| A-10 | —H | —H | —H | cycloheptyloxy | 107–108 |
| A-11 | —H | —H | —H | 1,2,3,4-tetrahydronaphthyl-1-oxy | 146–148 |
| A-12 | —H | —H | —H | —O—C(CF₃)Me | 127–128 |
| A-13 | —H | —H | —H | —O—CH₂CF₂CHF₂ | 125–126 |
| A-14 | —H | —H | —H | —O—CH₂CF₂CF₃ | 118–119 |
| A-15 | —H | —H | —H | —F | 142–143 |
| A-16 | —H | —H | —H | —Cl | 132–133 |
| A-17 | —H | —H | —H | —O—Ph | 169 |
| A-18 | —H | —H | —H | 4-Me-phenoxy | 178 |
| A-19 | —H | —H | —H | 3-Me-phenoxy | 97–99 |
| A-20 | —H | —H | —H | 4-Et-phenoxy | 133–135 |
| A-21 | —H | —H | —H | 3-Et-phenoxy | 67–69 |
| A-22 | —H | —H | —H | 3-(iso-Pr)-phenoxy | 92–94 |
| A-23 | —H | —H | —H | 3-(tert-Bu)-phenoxy | Amorphous solid |
| A-24 | —H | —H | —H | 4-OMe-phenoxy | 164–165 |
| A-25 | —H | —H | —H | 3-OMe-phenoxy | 112–114 |
| A-26 | —H | —H | —H | 3-OEt-phenoxy | 119–120 |
| A-27 | —H | —H | —H | 3-(O-n-Bu)-phenoxy | 114–115 |
| A-28 | —H | —H | —H | 3-OCF₃-phenoxy | 117–118 |
| A-29 | —H | —H | —H | 4-(OCHF₂)-phenoxy | 127–129 |
| A-30 | —H | —H | —H | 3-(OCHF₂)-phenoxy | 66–68 |
| A-31 | —H | —H | —H | 3-OPh-phenoxy | 136–138 |
| A-32 | —H | —H | —H | 3-F-phenoxy | 165–167 |
| A-33 | —H | —H | —H | 4-Cl-phenoxy | 183–184 |
| A-34 | —H | —H | —H | 3-Cl-phenoxy | 120–122 |
| A-35 | —H | —H | —H | 3-Br-phenoxy | 112–114 |
| A-36 | —H | —H | —H | 4-CF₃-phenoxy | 148–150 |
| A-37 | —H | —H | —H | 3-CF₃-phenoxy | 124–125 |
| A-38 | —H | —H | —H | 2-CF₃-phenoxy | 121–122 |
| A-39 | —H | —H | —H | 3-Ph-phenoxy | 47–49 |
| A-40 | —H | —H | —H | 3-(1,1-ethylenedioxyethyl)-phenoxy | 145–147 |
| A-41 | —H | —H | —H | 3-COMe-phenoxy | 122–123 |
| A-42 | —H | —H | —H | 4-COOMe-phenoxy | 185–186 |
| A-43 | —H | —H | —H | 3-COOMe-phenoxy | 114–116 |
| A-44 | —H | —H | —H | 4-SMe-phenoxy | 165–166 |

TABLE 2-continued

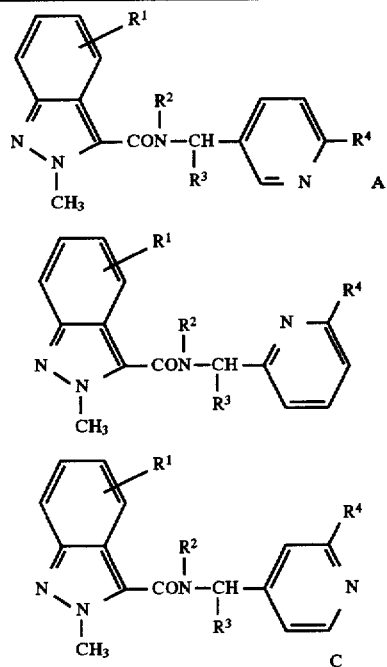

| Compound | R¹ | R² | R³ | R⁴ | m.p. (°C.) |
|---|---|---|---|---|---|
| A-45 | —H | —H | —H | 3-NO₂-phenoxy | 146–148 |
| A-46 | —H | —H | —H | 3-CN-phenoxy | 112–114 |
| A-47 | —H | —H | —H | 3,4-methylenedioxy-phenoxy | 152–154 |
| A-48 | —H | —H | —H | 2,3-dihyro-2,2-di-Me-benzo[b]furan-7-yl-oxy- | 142–144 |
| A-49 | —H | —H | —H | 2-naphthoxy | 136–137 |
| A-50 | —H | —H | —H | 1-naphthoxy | 137–139 |
| A-51 | —H | —H | —H | 6-Br-2-naphthoxy | 196–198 |
| A-52 | —H | —H | —H | 3,4-di-Me-phenoxy | 138–140 |
| A-53 | —H | —H | —H | 3,5-di-Me-phenoxy | 120–121 |
| A-54 | —H | —H | —H | 3,5-di-(iso-Pr)-phenoxy | 103–104 |
| A-55 | —H | —H | —H | 3,4-di-Cl-phenoxy | 139–141 |
| A-56 | —H | —H | —H | 2,4-di-Cl-phenoxy | 242–244 |
| A-57 | —H | —H | —H | 3-Cl-4-F-phenoxy | 144–146 |
| A-58 | -4-Cl | —H | —H | phenoxy | 100–102 |
| A-59 | -5-Cl | —H | —H | phenoxy | 189–191 |
| A-60 | -5-Cl | —H | —H | 4-CF₃-phenoxy | 182–184 |
| A-61 | -5-Cl | —H | —H | 3-CF₃-phenoxy | 130—131 |
| A-62 | -6-Cl | —H | —H | —O—Ph | 168–170 |
| A-63 | -7-Me | —H | —H | —O—Ph | 155–156 |
| A-64 | -7-Me | —H | —H | 4-Cl-phenoxy | 157–158 |
| A-65 | -7-Me | —H | —H | 4-CF₃-phenoxy | 158–160 |
| A-66 | -7-Me | —H | —H | 3-CF₃-phenoxy | 114–116 |
| A-67 | -7-Cl | —H | —H | —O—Ph | 155–157 |
| A-68 | -7-OMe | —H | —H | —O—Ph | 165–167 |
| A-69 | —H | —Me | —H | 3-CF₃-phenoxy | 1.5778* |
| A-70 | —H | —Et | —H | 3-CF₃-phenoxy | 1.5758* |
| A-71 | —H | —CH₂OMe | —H | 3-CF₃-phenoxy | 1.5750* |
| A-72 | —H | —COMe | —H | —O—CH(CF₃)Me | 1.5502* |
| A-73 | —H | —COMe | —H | 3-CF₃-phenoxy | 1.5789* |
| A-74 | —H | —H | —Me | 3-CF₃-phenoxy | 175–176 |
| A-75 | —H | —H | —H | —NH—Ph | 154–156 |
| A-76 | —H | —H | —H | —NH—3-Cl—Ph | 201 |
| A-77 | —H | —H | —H | —NH—4-CF₃—Ph | 235–236 |
| A-78 | —H | —H | —H | —NH—3-CF₃—Ph | 216–217 |
| A-79 | —H | —H | —H | —N(Me)—Ph | 155–157 |
| A-80 | —H | —H | —H | 1-pyrrolyl | 175–177 |
| A-81 | —H | —H | —H | 1-imidazolyl | 162–164 |
| A-82 | —H | —H | —H | 1-pyrrolidinyl | 175–176 |
| A-83 | —H | —H | —H | piperidino | 163–165 |
| A-84 | —H | —H | —H | 1,2,3,4-tetrahydro-2-isoquinolyl | 145–147 |
| B-1 | —H | —H | —H | —Cl | 146–147 |
| B-2 | —H | —H | —H | —O—Ph | 101–103 |
| B-3 | —H | —H | —H | 4-Me-phenoxy | 100–101 |

TABLE 2-continued

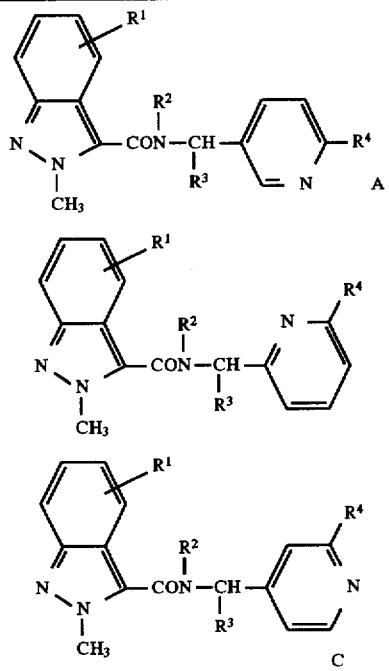

| Compound | R¹ | R² | R³ | R⁴ | m.p. (°C.) |
|---|---|---|---|---|---|
| B-4 | —H | —H | —H | 4-OMe-phenoxy | 133–134 |
| B-5 | —H | —H | —H | 4-Cl-phenoxy | 117–118 |
| B-6 | —H | —H | —H | 4-F-phenoxy | 102–103 |
| C-1 | —H | —H | —H | —O—Ph | 102–103 |
| C-2 | —H | —H | —H | 4-Cl-phenoxy | 132–134 |
| C-3 | —H | —H | —H | 4-Me-phenoxy | 150–151 |

The results of NMR and IR analyses of Compound A-17 were as follows:

$^1$H-NMR(CDCl$_3$) δppm: 1.23(9H,s),4.33(3H,s),4.56(2H, d), 6.81(1H,d),6.88(1H,dd),7.08(3H,m),7.21(3H,m),7.56 (1H,dd), 7.64(2H,m),8.12(1H,d) IR(KBr) cm$^{-1}$: 3400, 2960, 1655, 1600, 1580, 1520, 1475, 1425, 1395, 1365, 1250, 930

Examples of formulations of the agricultural and horticultural fungicides, insecticides, and/or miticides comprising the compounds of the present invention are explained below. However, the forms of the agricultural and horticultural pesticides of the present invention are not limited to the following examples.

Formulation Example 1

Wettable powder

A wettable powder containing 20% by weight of the active ingredient was prepared by uniformly mixing and pulverizing 20 parts by weight of the compound of the present invention, 20 parts by weight of Carplex #80 (trademark, white carbon, Shionogi & Co., Ltd.), 52 parts by weight of ST Kaolin Clay (trademark, kaolinite, Tsuchiya Kaolin Co., Ltd.), 5 parts by weight of Sorpol 9047K (trademark, anionic surfactant, Toho Kagaku Co., Ltd.) and 3 parts by weight of Runox P65L (trademark, anionic surfactant, Toho Kagaku Co., Ltd.).

Formulation Example 2

Dust

A dust containing 2% by weight of the active ingredient was prepared by uniformly mixing and pulverizing 2 parts by weight of a compound of the present invention, 93 parts by weight of clay (Nippon Talc Co., Ltd.) and 5 parts by weight of Carplex #80 (trademark, white carbon, Shionogi & Co., Ltd.).

Formulation Example 3

Emulsifiable Concentrate

An emulsifiable concentrate containing 20% by weight of the active ingredient was prepared by dissolving 20 parts by weight of a compound of the present invention in a mixed solvent consisting of 35 parts by weight of xylene and 30 parts by weight of dimethylformamide, and adding 15 parts by weight of Sorpol 3005X (trademark, the mixture of non-ionic surfactant and anionic surfactant, Toho Kagaku Co., Ltd. ) to the resulting solution.

Formulation Example 4

Flowable agent

A flowable agent containing 20% by weight of the active ingredient was prepared by pulverizing 30 parts by weight of the compound of the present invention, 5 parts by weight of Sorpol 9047K, 3 parts by weight of Solbon T-20 (trademark, non-ionic surfactant, Toho Kagaku Co., Ltd.), 8 parts by weight of ethylene glycol, and 44 parts by weight of water in the DYNO-Mill (Shinmaru Enterprises Co., Ltd.) in wet process, adding 10 parts by weight of aqueous solution of xanthan gum (natural polymer) to the resulting slurry mixture, and then mixing and dispersing the resulting mixture sufficiently.

Test Example 1

Insecticidal effect against the larvae of *Nilaparvata lugens*

Seedlings of rice plant were placed in a glass cylinder with 3 cm inner diameter and 17 cm height, and then, five larvae of four instar were put into the cylinder. Aqueous dilution (0.5 ml) of the agricultural and horticultural insecticide of the present invention prepared according to Formulation Example 3 was sprayed into the above glass cylinder (one concentration, two replicates) using a spraying tower (manufactured by Mizuho Rika, Co., Ltd.). Five days after the treatment, death and agony of the larvae were examined and the mortality (%) was calculated by counting one agonizing larva as being ½ death. The results are shown in Table 3 (Compound numbers in the table correspond to those described in Table 2.).

Test Example 2

Insecticidal effect agaist the larvae of *Plutella xylostella*

Slices of cabbage leaves (6 cm diameter) were immersed for one minute in the aqueous dilution of the agricultural and horticultural insecticide of the present invention prepared according to Formulation Example 1. The leaves were air-dried after the immersion, and then placed in a plastic cup (7 cm inner diameter). Five larvae of third instar were put in the cup (one concentration, two replicates). Four days after the introduction of the larvae, death and agony of the larvae were examined and the mortality (%) was calculated by counting one agonizing larva as being ½ death. The results are shown in Table 3 (Compound numbers in the table below correspond to those shown in Table 2).

TABLE 3

| Compound No. | Concentration (ppm) | Mortality (%) Nilaparvata lugens | Mortality (%) Plutella xylostella |
|---|---|---|---|
| A-1 | 500 | 100 | 100 |
| A-2 | " | " | " |
| A-3 | " | " | " |
| A-4 | " | " | " |
| A-5 | " | " | " |
| A-6 | " | " | 95 |
| A-7 | " | " | 100 |
| A-8 | " | " | " |
| A-9 | " | " | 95 |
| A-10 | " | " | 100 |
| A-12 | " | " | " |
| A-13 | " | " | " |
| A-14 | " | " | " |
| A-17 | " | " | " |
| A-18 | " | " | 95 |
| A-19 | " | " | 100 |
| A-20 | " | " | " |
| A-21 | " | 90 | 90 |
| A-24 | " | " | 100 |
| A-26 | " | 100 | " |
| A-29 | " | " | " |
| A-33 | " | " | " |
| A-36 | " | " | " |
| A-37 | " | " | " |
| A-38 | " | 90 | " |
| A-49 | " | 100 | " |

TABLE 3-continued

| Compound No. | Concentration (ppm) | Mortality (%) Nilaparvata lugens | Mortality (%) Plutella xylostella |
|---|---|---|---|
| A-63 | " | " | " |
| A-72 | " | " | " |
| B-2 | " | " | " |
| B-3 | " | " | " |

Test Example 3

Miticidal effect against the adults of *Tetranychus urticae*

Ten female adults of Tetranychus urticae were put on disks (3 cm diameter) of kidney bean leaf. The agricultural and horticultural miticide of the present invention prepared according to Formulation Example 1 was diluted with water up to the prescribed concentration. The resulting solution (3.5 ml) was sprayed onto the disks (one concentration, two replicates) using a rotary spraying tower (manufactured by Mizuho Rika Co., Ltd.). Twenty-four hours after the treatment, the dead larvae were counted and the miticidal rate (%) was calculated. The results are shown in Table 4.

Test Example 4

Miticidal effect against eggs of *Tetranychus urticae*

Five female adults of *Tetranychus urticae* were put on disks (3 cm diameter) of kidney bean leaf. The adults were allowed to oviposit for 20 hours, then the female adults were removed. The agricultural and horticultural miticide of the present invention prepared according to Formulation Example 1 was diluted with water up to the prescribed concentration. The resulting solution (3.5 ml) was sprayed onto the disks (one concentration, two replicates) using a rotary spraying tower (manufactured by Mizuho Rika CO., Ltd.). Eight days after the treatment, unhatched eggs and larvae after hatching were counted and the ovicidal rate (%) was calculated. The results are shown in Table 4.

TABLE 4

| Compound No. | Concentration (ppm) | Mitecidal rate (%) | Ovicidal rate (%) |
|---|---|---|---|
| A-1 | 500 | 100 | 90 |
| A-4 | " | " | " |
| A-9 | " | 95 | " |
| A-10 | " | 100 | 100 |
| A-12 | " | " | " |
| A-13 | " | " | " |
| A-36 | " | " | 70 |
| A-72 | " | " | 100 |

Test Example 5

Fungicidal effect against *Magnaporthe grisea*

Ten stocks of rice plant (species: Akinishiki) per pot were nursed by using resin pots of 6 cm diameter. The agricultural and horticultural fungicide (wettable powder) of the present invention prepared according to Formulation Example 1 was diluted with water up to the prescribed concentration, and then applied by foliage spraying onto the rice plants (3- to 4-leaf stages) in the amount of 10 ml per pot. After the sprayed solution was air-dried, a suspension of spores (5.0× $10^5$ spores/ml) obtained from the culture of *Magnaporthe grisea* in oatmeal cultivation medium was inoculated to the rice plants by spraying, and then, the pots were kept for 24 hours under a moist chamber at 25° C. Then, the pots were left for 7 days in a greenhouse (22° to 25° C.), and the numbers of appeared disease spots were measured and the preventive value was calculated from the following equation. The results are shown in Table 5.

TABLE 5

Preventive value (%) =

$$\frac{\text{(Numbers of disease spots per leaf in untreated pot)} - \text{(Numbers of disease spots per leaf in treated pot)}}{\text{Numbers of disease spots per leaf in untreated pot}} \times 100$$

| Compound No. | Concentration (ppm) | Preventive value(%) |
|---|---|---|
| A-2 | 250 | 94 |
| A-4 | " | 100 |
| A-6 | " | 91 |
| A-7 | " | 100 |
| A-10 | " | 100 |
| A-14 | " | 100 |
| A-16 | " | 90 |
| A-19 | " | 94 |
| A-26 | " | 100 |
| A-28 | " | 96 |
| A-29 | " | 100 |
| A-30 | " | 96 |
| A-34 | " | 90 |
| A-35 | " | 100 |
| A-37 | " | 100 |
| A-39 | " | 90 |
| A-45 | " | 100 |
| A-46 | " | 95 |
| A-49 | " | 100 |
| A-50 | " | 100 |
| A-57 | " | 92 |
| A-67 | " | 94 |
| A-69 | " | 94 |
| A-70 | " | 100 |
| A-71 | " | 100 |
| A-72 | " | 100 |
| B-1 | " | 95 |
| B-2 | " | 100 |
| B-3 | " | 100 |
| B-4 | " | 94 |
| C-1 | " | 100 |
| C-2 | " | 95 |

Test Example 6

Fungicidal effect against *Phytophthora infestans*

Three stocks of rice plant (species: Red Cherry) per pot were nursed by using resin pots of 6 cm diameter. The agricultural and horticultural fungicide (wettable powder) of the present invention prepared according to Formulation Example 1 was diluted with water up to the prescribed concentration, and then applied by foliage spraying onto the rice plants (3- to 4-leaf stages) in the amount of 10 ml per pot. After the sprayed solution was air-dried, a suspension of *zoosporangiums* (5.0×$10^4$ *zoosporangiums*/ml) obtained from the culture of *Phytophthora infestans* on sliced tomato leaves was inoculated onto the rice plants by spraying, and then the pots were kept in a moist chamber at 25 ° C. for 24 hours. Then, the pots were left for 4 days in a greenhouse (22° to 25 ° C.). The numbers of appeared disease spots in the leaves were measured and represented by disease indexes, and the preventive value was calculated from the following equation. The results are shown in Table 6.

TABLE 6

Disease index: 0: no disease spot was observed.
1: disease area was ⅓ or less.
3: disease area was from ⅓ to ⅔.
5: disease area was ⅔ or more.

$n_x$: Numbers of tomato leaves per pot having the disease index of x.

$$\text{Rate of disease (\%)} = \frac{(0 \times n_0 + 1 \times n_1 + 3 \times n_3 + 5 \times n_5)}{5(n_0 + n_1 + n_3 + n_5)} \times 100$$

$$\text{Preventive value (\%)} = \frac{\text{(Rate of disease in untreated pot)} - \text{(Rate of disease in treated pot)}}{\text{Rate of disease in untreated pot}} \times 100$$

| Compound No. | Concentration (ppm) | Preventive value (%) |
|---|---|---|
| A-1 | 250 | 100 |
| A-2 | 250 | 100 |
| A-3 | 250 | 100 |
| A-4 | 250 | 100 |
| A-5 | 250 | 100 |
| A-6 | 250 | 100 |
| A-7 | 250 | 100 |
| A-8 | 250 | 100 |
| A-9 | 250 | 100 |
| A-10 | 250 | 100 |
| A-11 | 250 | 92 |
| A-12 | 250 | 91 |
| A-13 | 250 | 100 |
| A-14 | 250 | 100 |
| A-16 | 250 | 100 |
| A-17 | 250 | 100 |
| A-18 | 250 | 90 |
| A-19 | 250 | 100 |
| A-20 | 250 | 100 |
| A-21 | 250 | 90 |
| A-24 | 250 | 93 |
| A-27 | 250 | 100 |
| A-29 | 250 | 100 |
| A-30 | 250 | 94 |
| A-32 | 250 | 100 |
| A-34 | 250 | 100 |
| A-36 | 250 | 100 |
| A-37 | 250 | 100 |
| A-40 | 250 | 92 |
| A-42 | 250 | 100 |
| A-43 | 250 | 94 |
| A-44 | 250 | 100 |
| A-46 | 250 | 100 |
| A-47 | 250 | 100 |
| A-48 | 250 | 100 |
| A-49 | 250 | 100 |
| A-51 | 250 | 100 |
| A-54 | 250 | 92 |
| A-55 | 250 | 92 |
| A-56 | 250 | 100 |
| A-57 | 250 | 100 |
| A-58 | 250 | 94 |
| A-60 | 250 | 93 |
| A-61 | 250 | 100 |
| A-64 | 250 | 100 |
| A-65 | 250 | 95 |
| A-67 | 250 | 100 |
| A-68 | 250 | 100 |
| A-69 | 250 | 100 |
| A-73 | 250 | 100 |
| B-3 | 250 | 100 |
| B-4 | 250 | 100 |
| B-5 | 250 | 93 |
| B-6 | 250 | 100 |
| C-1 | 250 | 96 |
| C-2 | 250 | 100 |

Test Example 7

By using Compounds No. A-1, A-2, A-3, A-4, A-5, A-8, A-17, A-29, A-33, A-36, A-37, A-42, A-47, A-49, A-64, A-65, B-3 and C-1 of the present invention, fungicidal effects against Phytophthora infestans were examined according to the method of Test Example 6, except that their concentrations were varied as shown in Table 7. As reference compounds, Compounds IV and V disclosed in the International Publication No. WO 94/5642 whose chemical structures are shown below.

TABLE 7

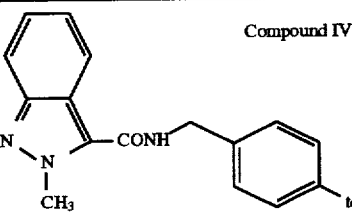

Compound IV

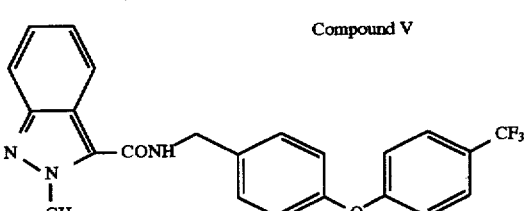

Compound V

| Compond No. | Concentration (ppm) | Preventive value (%) |
|---|---|---|
| IV | 250 | 35 |
| IV | 50 | 23 |
| IV | 10 | 0 |
| V | 250 | 84 |
| V | 50 | 47 |
| V | 10 | 0 |
| A-1 | 250 | 100 |
| A-1 | 50 | 100 |
| A-1 | 10 | 100 |
| A-2 | 250 | 100 |
| A-2 | 50 | 100 |
| A-2 | 10 | 95 |
| A-3 | 250 | 100 |
| A-3 | 50 | 100 |
| A-3 | 10 | 93 |
| A-4 | 250 | 100 |
| A-4 | 50 | 100 |
| A-4 | 10 | 100 |
| A-5 | 250 | 100 |
| A-5 | 50 | 100 |
| A-5 | 10 | 100 |
| A-8 | 250 | 100 |
| A-8 | 50 | 100 |
| A-8 | 10 | 95 |
| A-17 | 250 | 100 |
| A-17 | 50 | 100 |
| A-17 | 10 | 100 |
| A-29 | 250 | 100 |
| A-29 | 50 | 100 |
| A-29 | 10 | 100 |
| A-33 | 250 | 100 |
| A-33 | 50 | 96 |
| A-33 | 10 | 89 |
| A-36 | 250 | 100 |
| A-36 | 50 | 100 |
| A-36 | 10 | 100 |
| A-37 | 250 | 100 |
| A-37 | 50 | 96 |
| A-37 | 10 | 85 |
| A-42 | 250 | 100 |
| A-42 | 50 | 100 |
| A-42 | 10 | 91 |
| A-47 | 250 | 100 |
| A-47 | 50 | 100 |
| A-47 | 10 | 88 |
| A-49 | 250 | 100 |
| A-49 | 50 | 100 |

TABLE 7-continued

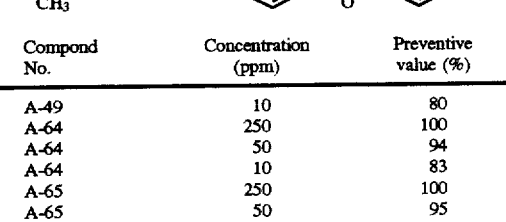

Compound IV

Compound V

| Compond No. | Concentration (ppm) | Preventive value (%) |
|---|---|---|
| A-49 | 10 | 80 |
| A-64 | 250 | 100 |
| A-64 | 50 | 94 |
| A-64 | 10 | 83 |
| A-65 | 250 | 100 |
| A-65 | 50 | 95 |
| A-65 | 10 | 80 |
| B-3 | 250 | 100 |
| B-3 | 50 | 95 |
| B-3 | 10 | 89 |
| C-1 | 250 | 100 |
| C-1 | 50 | 95 |
| C-1 | 10 | 85 |

From the foregoing description, it can be understood that the indazole compounds of the present invention have extremely high controlling effects against various types of phytopathogenic fungi, harmful insects, and mites, and thus, they are useful as active ingredients of agricultural and horticultural fungicides, insecticides, and miticides.

What is claimed is:

1. An indazole compound represented by the following formula:

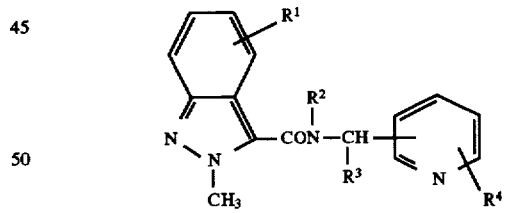

wherein $R^1$ represents a hydrogen atom, a $C_1$–$C_4$ alkyl group, a $C_1$–$C_4$ alkoxy group, or a halogen atom; $R^2$ represents a hydrogen atom, a $C_1$–$C_4$ alkyl group, a $C_2$–$C_5$ alkanoyl group, methoxymethyl group, or 2-methoxy ethyl group, a $C_2$–$C_5$ alkanoyl group, methoxymethyl group, or 2-methoxy ethyl group; $R^3$ represents a hydrogen atom or a $C_1$–$C_4$ alkyl group; $R^4$ represents a hydrogen atom, a $C_1$–$C_8$ alkyl group, a $C_1$–$C_8$ alkoxy group, a halogen atom, a $C_1$–$C_4$ haloalkoxy group, a 5-membered to 7-membered cycloalkoxy group which may be substituted, a $C_1$–$C_4$ alkylthio group, a phenylamino group which may be substituted, an N-($C_1$–$C_4$ alkyl)-phenylamino group, pyrrolyl group, imidazolyl group, pyrrolidino group, a piperidino group which may be substituted, or a phenoxy group which may be substituted, and where a functional group selected from the group consisting of said cycloalkoxy, phenylamino, piperidino, and phenoxy groups has two or more substituents on its nucleus, any two adjacent substituents among said substituents may form a ring structure together with two atoms on the nucleus to which the adjacent substituents bind, and said ring structure may further has one more substitutents on the ring.

2. The indazole compounds according to claim 1, wherein $R^4$ is a hydrogen atom, a $C_1-C_8$ alkyl group, a $C_1-C_8$ alkoxy group, a halogen atom, a $C_1-C_4$ haloalkoxy group, a 5- to 7-membered cycloalkoxy group which may optionally have one or more $C_1-C_4$ alkyl groups or a condensed benzene ring, a phenylamino group which may optionally have one or more halogen atoms or one or more $C_1-C_4$ haloalkyl group, an N-($C_1-C_4$ alkyl)-phenylamino group, pyrrolyl group, imidazolyl group, pyrrolidino group, a piperidino group which may optionally have a condensed benzene ring, or a phenoxy group which may optionally have one to three substituents selected from the group consisting of a $C_1-C_8$ alkyl group, a $C_1-C_8$ alkoxy group, a halogen atom, nitro group, cyano group, a $C_1-C_4$ haloalkyl group, a $C_1-C_4$ haloalkoxy group, phenyl group, phenoxy group, a $C_2-C_5$ alkanoyl group whose oxo group may be protected with a ketal group, benzoyl group, a $C_1-C_4$ alkoxycarbonyl group, a $C_1-C_4$ alkylthio group, trifluoromethylthio group, and methylenedioxy group and where said phenoxy group has two or three substituents, the substituents may be the same or different, and the benzene ring of said phenoxy group may have a condensed benzene ring which ring may further be substituted with one or more halogen atoms or one or more $C_1-C_4$ alkoxy groups or a condensed saturated furan ring which ring may further be substituted with one or more $C_1-C_4$ alkyl groups.

3. The indazole compound according to claim 1, wherein $R^4$ is a $C_1-C_8$ alkyl group, a $C_1-C_4$ alkoxy group, a halogen atom, a $C_1-C_4$ haloalkoxy group, a 5- to 7-membered cycloalkoxy group which may optionally have one or more $C_1-C_4$ alkyl groups or one condensed benzene ring, a phenylamino group which may optionally have one or more halogen atoms or one or more $C_1-C_4$ haloalkyl groups, an N-($C_1-C_4$ alkyl)-phenylamino group, pyrrolyl group, imidazolyl group, pyrrolidino group, a piperidino group which may optionally have one condensed benzene ring, or a phenoxy group which may optionally have one to three substituents selected from the group consisting of a $C_1-C_8$ alkyl group, a $C_1-C_8$ alkoxy group, a halogen atom, nitro group, cyano group, a $C_1-C_4$ haloalkyl group, a $C_1-C_4$ haloalkoxy group, phenyl group, phenoxy group, a $C_2-C_5$ alkanoyl group whose oxo group may be protected with a ketal group, a $C_1-C_4$ alkoxycarbonyl group, a $C_1-C_4$ alkylthio group, and methylenedioxy group (where said phenoxy group has two or three substituents, the substituents may be the same or different), and the benzene ring of said phenoxy group may have one condensed benzene ring the benzene ring of the phenoxy group may have one condensed benzene ring which ring may further be substituted with one or more halogen atoms or one condensed saturated furan ring which ring may further be substituted with one or more $C_1-C_4$ alkyl groups.

4. The indazole compound according to claim 1, wherein $R^4$ is a $C_1-C_8$, alkyl group, a $C_1-C_4$ alkoxy group, a halogen atom, a $C_1-C_4$ haloalkoxy group, a 5- to 7-membered cycloalkoxy group which may optionally have one $C_1-C_4$ alkyl group or one condensed benzene ring, a phenylamino group which may optionally have one halogen atom or one $C_1-C_4$ haloalkyl group, an N-($C_1-C_4$ alkyl)-phenylamino group, pyrrolyl group, imidazolyl group, pyrrolidino group, a piperidino group which may optionally have one condensed benzene ring, or a phenoxy group which may optionally have one or two substituents selected from the group consisting of a $C_1-C_8$ alkyl group, a $C_1-C_8$ alkoxy group, a halogen atom, nitro group, Cyano group, a $C_1-C_4$ haloalkyl group, a $C_1-C_4$ haloalkoxy group, phenyl group, phenoxy group, a $C_2-C_5$ alkanoyl group whose oxo group may be protected with a ketal group, a $C_1-C_4$ alkoxycarbonyl group, a $C_1-C_4$ alkylthio group, and a methylenedioxy group and where said phenoxy group has two substituents, the substituents may be the same or different, and the benzene ring of said phenoxy group may have one condensed benzene ring which ring may further be substituted with one halogen atom or one condensed saturated furan ring which ring may further be substituted with one $C_1-C_4$ alkyl group.

5. The indazole compound according to claim 1, wherein $R^2$ and $R^3$ are hydrogen atoms. compounds represented by general formula (II) and general formula (III) can be prepared by methods which are known to those skilled in the art.

6. An agricultural and horticultural pesticide which comprises an effective amount of an indazole compound represented by the formula

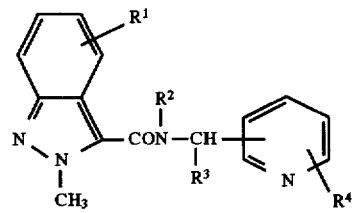

wherein $R^1$ represents a hydrogen atom, a $C_1-C_4$ alkyl group, a $C_1-C_4$ alkoxy group, or a halogen atom; $R^2$ represents a hydrogen atom, a $C_1-C_4$ alkyl group, a $C_2-C_5$ alkanoyl group, methoxymethyl group, or 2-methoxy ethyl group; $R^3$ represents a hydrogen atom or a $C_1-C_4$ alkyl group; $R_4$ represents a hydrogen atom, a $C_1-C_4$ alkyl group, a $C_1-C_4$ alkoxy group, a halogen atom, a $C_1-C_4$ haloalkoxy group, a 5-membered to 7-membered cycloalkoxy group which may be substituted, a $C_1-C_4$ alkylthio group, a phenylamino group which may be substituted, an N-($C_1-C_4$ alkyl)-phenylamino group, pyrrolyl group, imidazolyl group, pyrrolidino group, a piperidino group which may be substituted, or a phenoxy group which may be substituted, and where a functional group selected from the group consisting of said cycloalkoxy, phenylamino, piperidino, and phenoxy groups has two or more substituents on its nucleus, any two adjacent substituents among said substituents may form a ring structure together with two atoms on the nucleus to which the adjacent substituents bind, and said ring structure may further has one or more substitutents on the ring, and an agrochemical adjuvant therefor.

7. An agricultural and horticultural pesticide according to claim 6 wherein $R^4$ is a $C_1-C_8$ alkyl group, a $C_1-C_4$ alkoxy group, a halogen atom, a $C_1-C_4$ haloalkoxy group, a 5- to 7-membered cycoalkoxy group which may optionally have one or more $C_1-C_4$ alkyl groups or one condensed benzene ring, a phenylamino group which may optionally have one or more halogen atoms or one or more $C_1-C_4$ haloalkyl groups, an N-($C_1-C_4$ alkyl)-phenylamino group, pyrrolyl group, imidazolyl group, pyrrolidino group, a piperidino group which may optionally have one condensed benzene ring, or a phenoxy group which may optionally have one to three substituents selected from the group consisting of a $C_1$–$C_8$ alkyl group, a $C_1$–$C_4$ alkoxy group, a halogen atom, nitro group, cyano group, a $C_1$–$C_4$ haloalkyl group, a $C_1$–$C_4$ haloalkoxy group, phenyl group, phenoxy group, a $C_2$–$C_5$ alkanoyl group whose oxo group may be protected with a ketal group, a $C_1$–$C_4$ alkoxycarbonyl group, a $C_1$–$C_4$ alkylthio group, and methylenedioxy group and where said phenoxy group has two or three substituents, the substituents may be the same or different, and the benzene ring of said phenoxy group may have one condensed benzene ring which ring may further be substituted with one or more halogen atoms or one condensed saturated furan ring which ring may further be substituted with one or more $C_1$–$C_4$ alkyl groups.

* * * * *